(12) United States Patent
Fan

(10) Patent No.: US 11,998,646 B2
(45) Date of Patent: Jun. 4, 2024

(54) HEATING DEVICE AND METHOD FOR HEATING AND STERILIZING CANS

(71) Applicant: Linxiao Fan, Hebei (CN)

(72) Inventor: Linxiao Fan, Hebei (CN)

( * ) Notice: Subject to any disclaimer, the term of this patent is extended or adjusted under 35 U.S.C. 154(b) by 0 days.

(21) Appl. No.: 18/515,674

(22) Filed: Nov. 21, 2023

(65) Prior Publication Data
US 2024/0108768 A1    Apr. 4, 2024

Related U.S. Application Data

(63) Continuation of application No. PCT/CN2023/102608, filed on Jun. 27, 2023.

(30) Foreign Application Priority Data

Sep. 30, 2022   (CN) .......................... 202211214080.1

(51) Int. Cl.
*A61L 2/04*       (2006.01)
*A61L 2/26*       (2006.01)

(52) U.S. Cl.
CPC ........ *A61L 2/04* (2013.01); *A61L 2/26* (2013.01); *A61L 2202/122* (2013.01); *A61L 2202/123* (2013.01); *A61L 2202/17* (2013.01); *A61L 2202/23* (2013.01)

(58) Field of Classification Search
CPC ........ A61L 2/04; A61L 2/26; A61L 2202/122; A61L 2202/123; A61L 2202/17; A61L 2202/23
See application file for complete search history.

(56) References Cited

FOREIGN PATENT DOCUMENTS

| CH | 129286    A  | 12/1928 |
|----|--------------|---------|
| CN | 201758744 U | 3/2011  |
| CN | 107242286 A | 10/2017 |
| CN | 207411426 U | 5/2018  |
| CN | 213756567 U | 7/2021  |
| GB | 622939 A    | 5/1949  |
| RU | 2342052 C1  | 12/2008 |

OTHER PUBLICATIONS

International Search Report of corresponding PCT application No. PCT/CN2023/102608; 4 Pgs.; Oct. 14, 2023.

*Primary Examiner* — Sean E Conley
(74) *Attorney, Agent, or Firm* — Cooper Legal Group, LLC

(57) ABSTRACT

A method for heating and sterilizing cans, including the following steps: Step 1: placing one or more cans in the cage body successively along an axis direction, and clamping the one or more cans in the cage body; Step 2: adding hot oil in the storage tank, and maintaining an oil temperature; Step 3: placing the cage body in the storage tank, and driving the cage body to roll in the storage tank by the drive assembly until the cage body enters the transition box; Step 4: conveying the cage body in the transition box, and introducing hot air or cold air into the transition box, until the cage body leaves the transition box through the discharge port; and Step 5: taking out the one or more cans from the cage body, and cleaning the one or more cans.

1 Claim, 6 Drawing Sheets

HEATING DEVICE AND METHOD FOR HEATING AND STERILIZING CANS

CROSS-REFERENCE TO RELATED APPLICATION

This application is a continuation of PCT application serial no. PCT/CN2023/102608, filed on Jun. 27, 2023, which claims the priority and benefit of Chinese patent application serial no. 202211214080.1, filed on Sep. 30, 2022. The entireties of PCT application serial no. PCT/CN2023/102608 and Chinese patent application serial no. 202211214080.1 are hereby incorporated by reference herein and made a part of this specification.

FIELD OF THE INVENTION

The present application relates to the field of can production, in particular to a can fixing cage, a heating device and a method for heating and sterilizing cans.

DESCRIPTION OF RELATED ART

A can is a sealable container made of metal sheet, glass, plastic, cardboard, or a combination of the above materials, containing commercial food, which is specially treated, formulated, canned, sealed, sterilized, cooled, or aseptically filled, to meet the requirements of commercial sterility, and can be kept at room temperature for a long time without spoilage.

There are two key features in canning: seal and sterilization. Steam sterilization technology is usually adopted for canned food packaged by metal sheets to make canned food reach the standard of absolute sterility.

In the related technologies mentioned above, the processing period for sterilizing the cans by steam in a sterilization cauldron is relatively long, which will affect the taste and nutrition of the food inside the cans due to the long processing period.

BRIEF SUMMARY OF THE INVENTION

In order to improve the sterilization efficiency of cans and reduce the processing period, the present application provides a can fixing cage, a heating device, and a method for heating and sterilizing cans.

In a first aspect, the present application provides a tank reinforcement cage, which adopts the following technical solution:

a can fixing cage, including a cage body for holding cans, in which the cage body has an opening at one end, and the can fixing cage further includes a cage cover configured for sealing the opening of the cage body; in particular, the cage cover and the cage body are detachably connected, and both ends of the cans abut against pad blocks, and the cans are fixed by the pad blocks in the cage body.

In the above technical solution, a plurality of cans can be placed end to end inside the cage body, and the cans are separated by pad blocks. At the same time, the side walls of the head end and tail end of the can abut against adjacent pad blocks, and the cans are pressed by the cage cover, such that the pad blocks and the cans are tightly connected. With such a setting, a plurality of cans inside the cage body can be heated at the same time, and the cans are directly heated by the heat source, so that the temperature of the cans be rapidly raised in a short period. Under the limitation of the cage body, the cage cover, and the pad blocks, the cans will not expand and burst due to the increase of internal air pressure under heating, so the sterilization temperature can be reached quickly, the period for heating and sterilizing is shorten, and the sterilization efficiency is improved, while maintaining the taste and nutrition of the food inside the cans.

In some embodiments, a slider is provided on the sidewalls of the edge of the pad blocks, and a sliding slot configured to be parallel to a centerline of the can fixing cage is formed in the inner wall of the can fixing cage, and the slider is slidably connected in the sliding slot.

In the above technical solution, the pad block is slidably connected with the cage body by the slider, and under the cooperation of the slider and the sliding slot, the pad block remains on the centerline of the cage body, so that it can be quickly aligned and abut against the ends of the cans, improving the installation efficiency.

In some embodiments, a positioning block configured to be inserted into the sliding slot is provided on the sidewall of the edge of the cage cover, and a bolt is threaded through the positioning block, and an end of the bolt abuts against a slot bottom of the sliding slot.

In the above technical solution, the cage cover can slide relative to the cage body, so that the number of cans inside the cage body can be adjusted. After the cage cover is pressed against the pad blocks, the cage cover and the cage body are fixedly connected by bolts to maintain the overall stability, while improving the convenience of using the can fixing cage.

In some embodiments, a connecting bolt is provided at an end of the cage body away from the opening, and the connecting bolt is connected with another cage cover. When the opening of the adjacent cage body is closed by the cage cover, the cage cover and the cage body are connected by the connecting bolt.

In the above technical solution, the cage body and the cage cover are made to be a whole by the connecting bolt. When the cans are placed inside the cage body, another cage cover can cover the opening of the cage body and fix the cans inside the cage body, so that the two cages are connected and are on the same axis, so that the cages are connected in sequence. According to the actual situation, a plurality of cans can be arranged in sequence and heated at the same time to improve work efficiency.

In a second aspect, the present application provides a heating device for heating a can fixing cage, which adopts the following technical solution:

a heating device for heating a can fixing cage, including a heating box with an opening on an upper end face, in particular, a storage tank is provided inside the heating box, the can fixing cage is arranged in the storage tank, a drive assembly configured for driving a movement of the can fixing cage is provided in the storage tank, and a heater is provided below the storage tank; in particular, the can fixing cage includes a cage body configured for holding cans, the cage body has an opening at one end, and the can fixing cage further includes a cage cover configured for sealing the opening of the cage body; in particular, the cage cover and the cage body are detachably connected, and both ends of the cans abut against pad blocks, and the cans are fixed by the pad blocks in the cage body.

In the above technical solution, hot oil is stored in the storage tank, and the temperature of the hot oil is maintained by the heater. After the can fixing cage holding the cans is put into the hot oil, and the can fixing cage is driven to roll by the drive assembly, and During the process that the can fixing cage rolls from one end of the storage tank to the other end of the storage tank, the cans are directly heated by the hot oil, which can quickly increase the temperature of the cans. Moreover, the temperature of the hot oil is easy to adjust, reducing the possibility of food damage inside the can due to excessive temperature. Therefore, the cans are able to be sterilized quickly, while maintaining the taste and nutrition of the food inside the cans.

In some embodiments, the drive assembly includes a transmission chain; in which a first side of the transmission chain is located above the storage tank, a second side of the transmission chain is located below the storage tank, transmission sprockets configured for meshing with an inner side of the transmission chain are provided outside two ends of the storage tank, the heating box is provided with a drive motor configured for driving the transmission sprockets to rotate, and a plurality of pushing components distributed evenly are provided on the transmission chain, and the can fixing cage is located between two adjacent pushing components.

In the above technical solution, the transmission sprockets is driven to rotate by the driving motor, so that the pushing component is driven to move by the transmission chain, and the can fixing cage between two adjacent pushing components is pushed by the pushing component, thereby the can fixing cage and the cans are driven to roll in hot oil, the cans are evenly heated, and at the same time, the food inside the cans keeps rolling during the rolling process, which further improves the uniformity of heating, the sterilization efficiency, and product quality.

In some embodiments, a first oil guide groove parallel to the transmission chain is formed in an inner bottom wall of the storage tank, second oil guide grooves are further formed in the inner bottom wall of the storage tank at both sides of the first oil guide groove, the first oil guide groove and the second oil guide grooves are configured to be parallel with each other, the first oil guide groove has a gradually decreasing groove depth from a first end to a second end of the first oil guide groove, the second oil guide groove has a gradually increasing groove depth from a first end to a second end of the first oil guide groove.

In the above technical solution, when the can fixing cage enters the storage tank at a deeper end of the first oil guide groove, and rolls toward a shallower end of the first oil guide groove, the hot oil in the first oil guide groove is driven to move as the cans. At this time, the hot oil in a shallower part of the second oil guide groove flows to a deeper part of the first oil guide groove, and at the same time, the hot oil flows from a deeper part of the second oil guide groove to a shallower part of the second oil guide groove. Therefore, during the moving process of the cans, the hot oil circulates in the storage tank, thereby reducing the temperature fluctuation of the hot oil and improving the heating effect to the cans.

In some embodiments, a transition box is provided outside one end of the heating box, a feed port is provided in the transition box at a first side close to the heating box, and a discharge port is provided in the transition box at a second side far away from the heating box, a lower side wall of the feed port is provided with a guide plate configured for receiving the can fixing cage, one end of the guide plate away from the feed port is configured to be inclined upward and close to the heating box, the transition box is provided with a conveyor belt configured for connecting the feed port and the discharge port, and the transition box is provided with a ventilation pipe.

In the above technical solution, when the cans reach the inside of the transition box, the heat emitted by the cans will increase the temperature inside the transition box, thereby maintaining the temperature of the cans, so that the cans continue to heat the food inside at a certain temperature, improving the product quality. In addition, when the heat emitted by the cans itself cannot reach the appropriate temperature in the transition box, the hot or cold air is passed into the transition box through the ventilation pipe to adjust the temperature and improve the stability.

In a third aspect, the present application provides a method for heating and sterilizing cans, which adopts the following technical solution:

a method for heating and sterilizing cans, including the following steps:

Step 1: placing one or more cans in the cage body successively along an axis direction, and clamping the one or more cans in the cage body by the cage cover;

Step 2: adding hot oil in the storage tank, and maintaining an oil temperature by using the heater;

Step 3: placing the cage body in the storage tank, and driving the cage body to roll in the storage tank by the drive assembly until the cage body enters the transition box;

Step 4: conveying the cage body in the transition box, and introducing hot air or cold air into the transition box through the ventilation pipe to maintain the one or more cans inside the cage body at an appropriate temperature, until the cage body leaves the transition box through the discharge port; and Step 5: taking out the one or more cans from the cage body, and cleaning the one or more cans.

In summary, the present application can achieve at least one of the following beneficial technical effects:

1. the cans are fixed and protected by the can fixing cage, so that the cans can be heated up quickly in a short period of time without damage, improving the sterilization efficiency of the cans and improving the product quality at the same time;

2. the cans are heated directly through hot oil heated by the heater, such that the heating temperature can be accurately controlled and the heating stability is improved.

DETAILED DESCRIPTION

The present application will be described in further detail below with reference to FIGS. 1-6.

Embodiment 1 of the present application discloses a can fixing cage.

Embodiment 1

Figure 1:
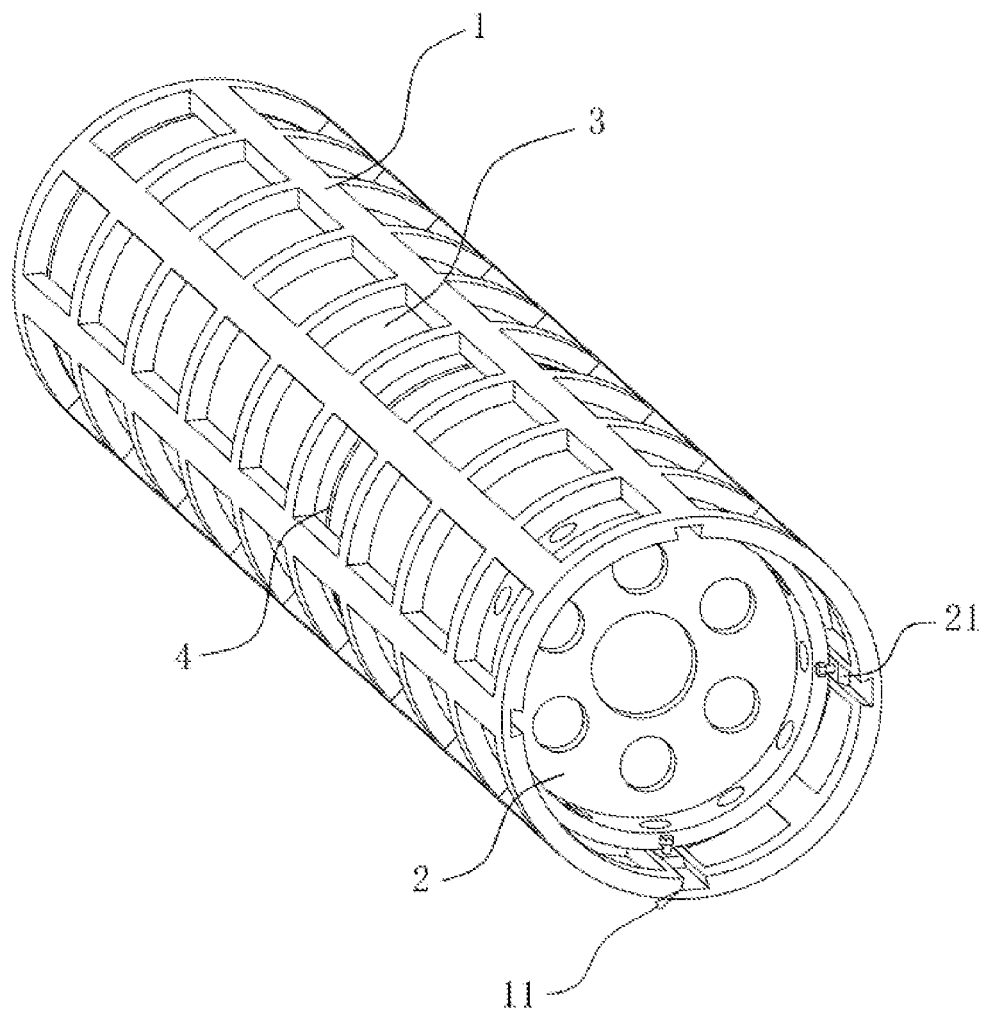
FIG. 1 is a schematic structural diagram of a can fixing cage in Embodiment 1 of the present application.
Figure 2:
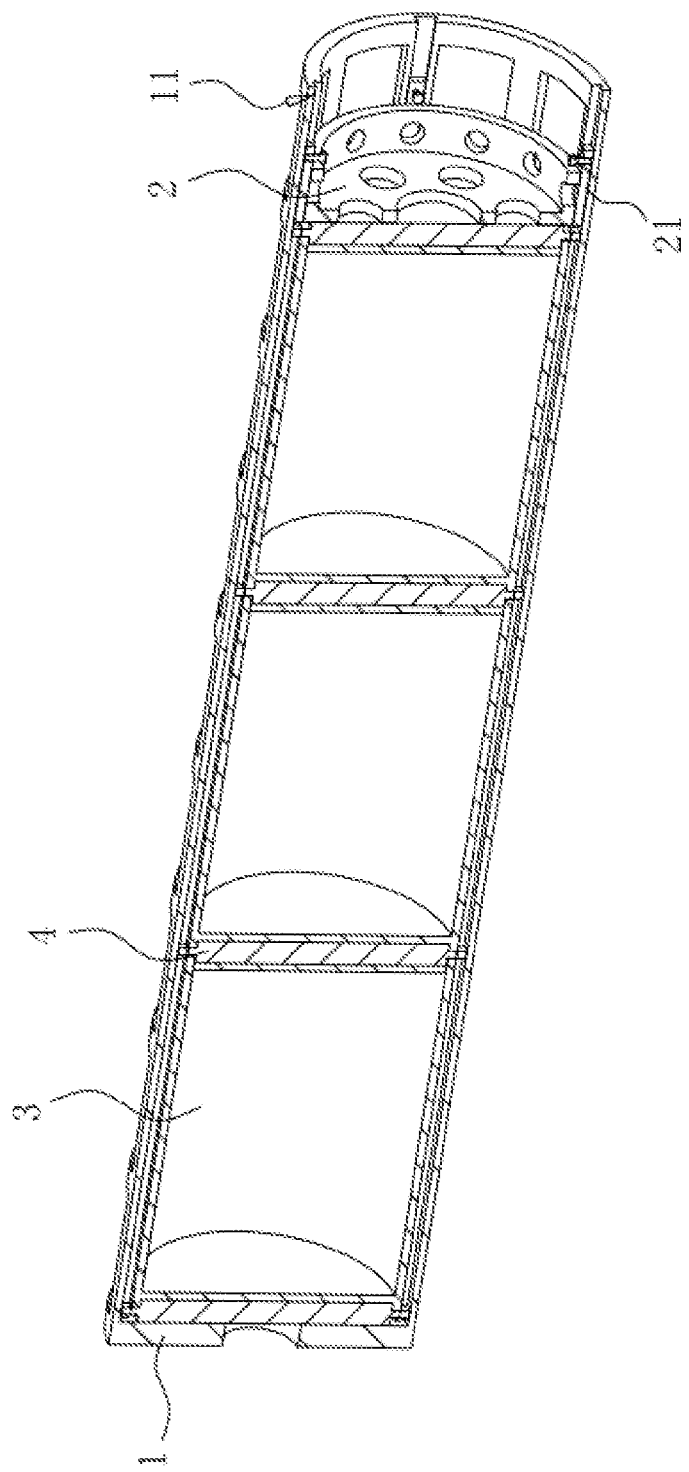
FIG. 2 is a schematic diagram of the internal structure of the can fixing cage.
Figure 3:
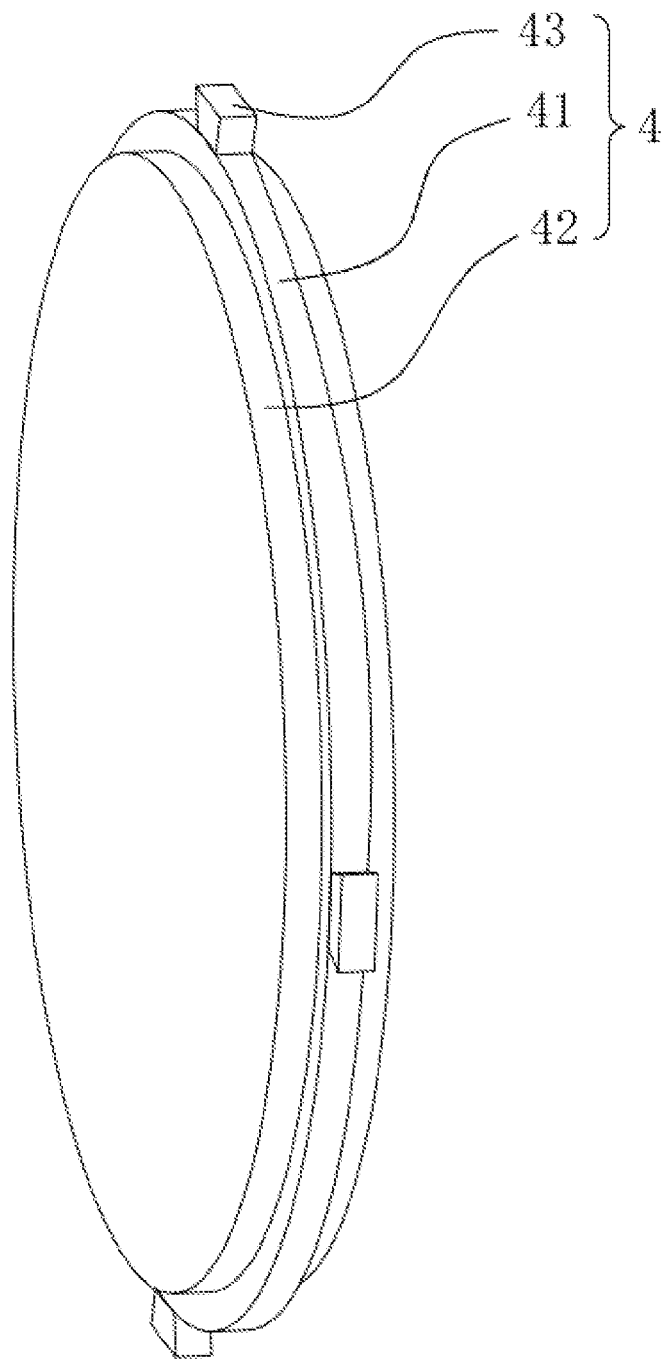
FIG. 3 is a structural schematic diagram of the pad block.

Referring to FIG. 1, the can fixing cage includes a cylindrical cage body 1 with a grid structure, and the cage body 1 has an opening at one end. Referring to FIGS. 2 and 3, a plurality of cans 3 can be set inside the cage body 1 at the same time, the cans 3 are distributed along the axis of the cage body 1 in sequence, and the outer walls of the cans 3 abut against the inner wall of the cage body 1. Pad blocks 4 are provided between two adjacent cans 3. The pad block 4 includes a support block 41 coaxial with the cage body 1, and the side wall of the edge of the support block 41 abut against the inner side walls of the cage body 1. Abutting blocks 42 that are coaxial are fixed on the side walls of the support blocks 41 close to the can 3, and the side of the abutting block 42 away from the support block 41 abuts against the end of the can 3.

In order to facilitate placing the cans 3 into the cage body 1, a plurality of sliding slots 11 parallel to the axis of the cage body 1 are formed in the inner wall of the cage body 1, and the plurality of sliding slots 11 are evenly distributed around the axis of the cage body 1. The sliding slot 11 is configured to run to the opening. A sliders 43 corresponding to the sliding slot 11 is fixed on the side wall of the edge of the support block 41. The slider 43 is configured to be inserted into the sliding slot 11 from the opening, and is slidably connected with the cage body 1 along the sliding slot 11. In particular, the slider 43 and the sliding slot 11 are both configured to be dovetail shaped.

A cage cover 2 is provided at the opening of the cage body 1, and the cage cover 2 has the same diameter as the support block 41. The side wall of the edge of the cage cover 2 is provided with a positioning block 21 configured to be inserted in the sliding slot 11. One end of the positioning block 21 extends towards the opening along the direction parallel to the sliding slot 11. Bolts are inserted the positioning block 21, and the bolts are threadedly connected with the positioning block 21, and one end of the bolt passing through the positioning block 21 abuts against the groove bottom of the sliding slot 11.

The implementation principle of Embodiment 1 is as follows: a pad block 4 is put into the cage body 1 firstly, then a can 3 is put into the cage body 1, such that the pad block 4 abuts against the side wall of the end of the can 3. Then, the pad block 4 and the can 3 are put into the cage body 1 successively. This process is repeated until a rated number of cans 3 are reached, and ended with a pad block 4. And a cage cover 2 is arranged on the cage body 1, and the cage cover 2 abuts against and compresses the pad block 4, thereby all the cans 3 are fixed, and the cage cover 2 is fixed on the cage body 1 by bolts. The fixing of the cans 3 are completed.

Embodiment 2

Figure 4:
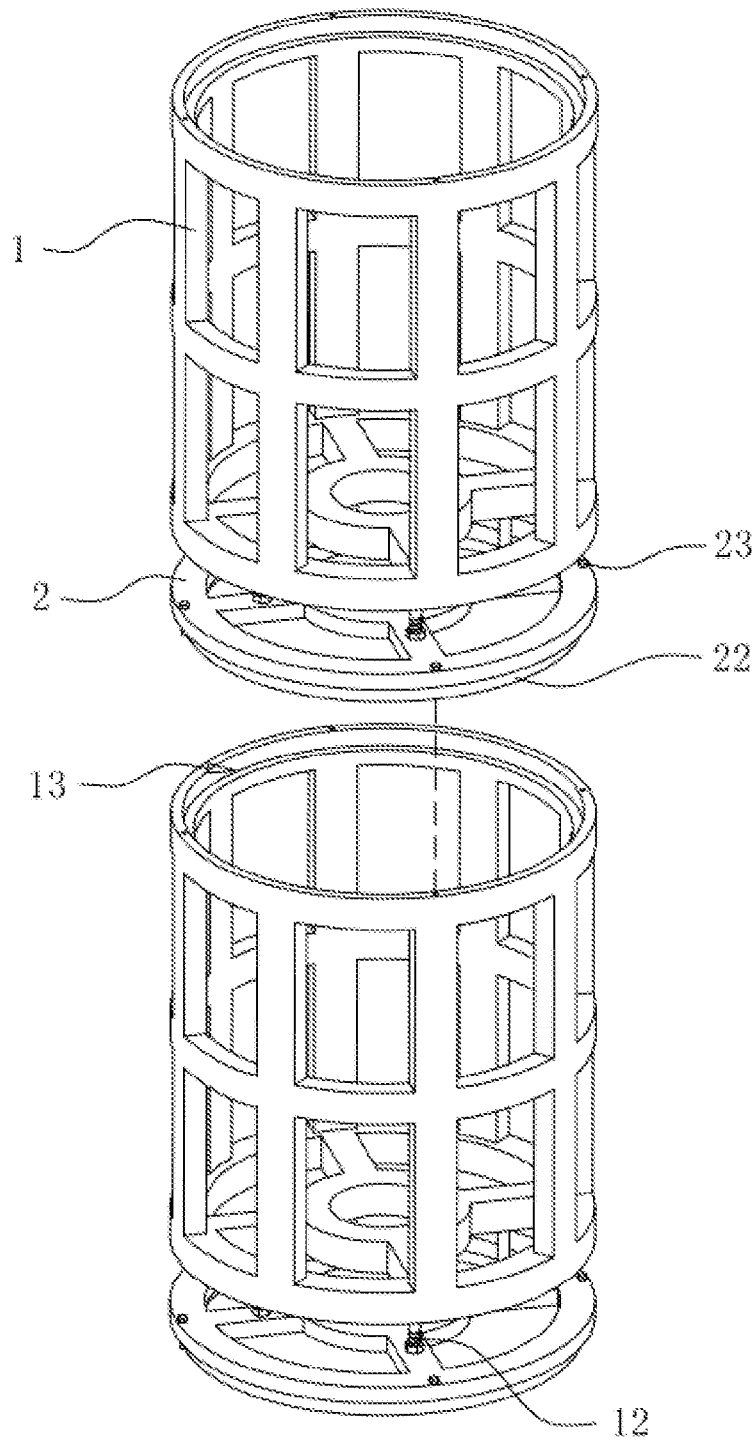
FIG. 4 is a schematic structural diagram of the can fixing cage of Embodiment 2 of the present application.

Referring to FIG. 4, the difference between Embodiment 2 and Embodiment 1 is that one end of the cage body 1 far away from the opening is fixed with a plurality of connecting bolts 12 evenly distributed around the centerline of the cage body 1, and the cage cover 2 is provided with connecting holes corresponding to the connecting bolts 12. The connecting bolt 12 passes through the cage cover 2, and two connecting nuts are screwed on the connecting bolt 12, and the two connecting nuts are located on two sides of the cage cover 2, respectively. A countersink groove is formed in the cage cover 2 on a side away from the cage body 1, and the connecting nut is located in the countersink groove.

A limit groove 13 is formed in the inner wall of the cage body 1 at the opening, and the limit groove 13 runs around the axis of the cage body 1. And cage cover 2 is fixed with a limit block 22 corresponding to the limit groove 13 at a side away from the cage body 1.

When the cage cover 2 faces the opening of another cage body 1, the cage cover 2 is engaged with opening of another cage body 1, and the limit block 22 is inserted into the limit groove 13 of another cage body 1. The fixing bolts 23 penetrate the edge of the cage cover 2. The fixing bolts 23 are parallel to the center line of the cage cover 2, the fixing bolts 23 penetrate into the cage body 1 at the same time, and are threaded with the cage body 1, thereby the cage cover 2 is fixed on the cage body 1, and the two cage bodies 1 are connected.

The implementation principle of Embodiment 2 is as follows: pad blocks 4 are placed on both sides of the cans 3, and the pad blocks 4 are placed in the cage body 1 along with the cans 3, and then the cage cover 2 is fixed at the opening of the cage body 1, so that the can 3 is fixed, and the two cage bodies 1 are connected as a whole. Then the cans 3 are placed in another cage body 1, and the above process is repeated to fix the cans 3 successively.

Embodiment 3 of the present application discloses a heating device.

Embodiment 3

Figure 5:
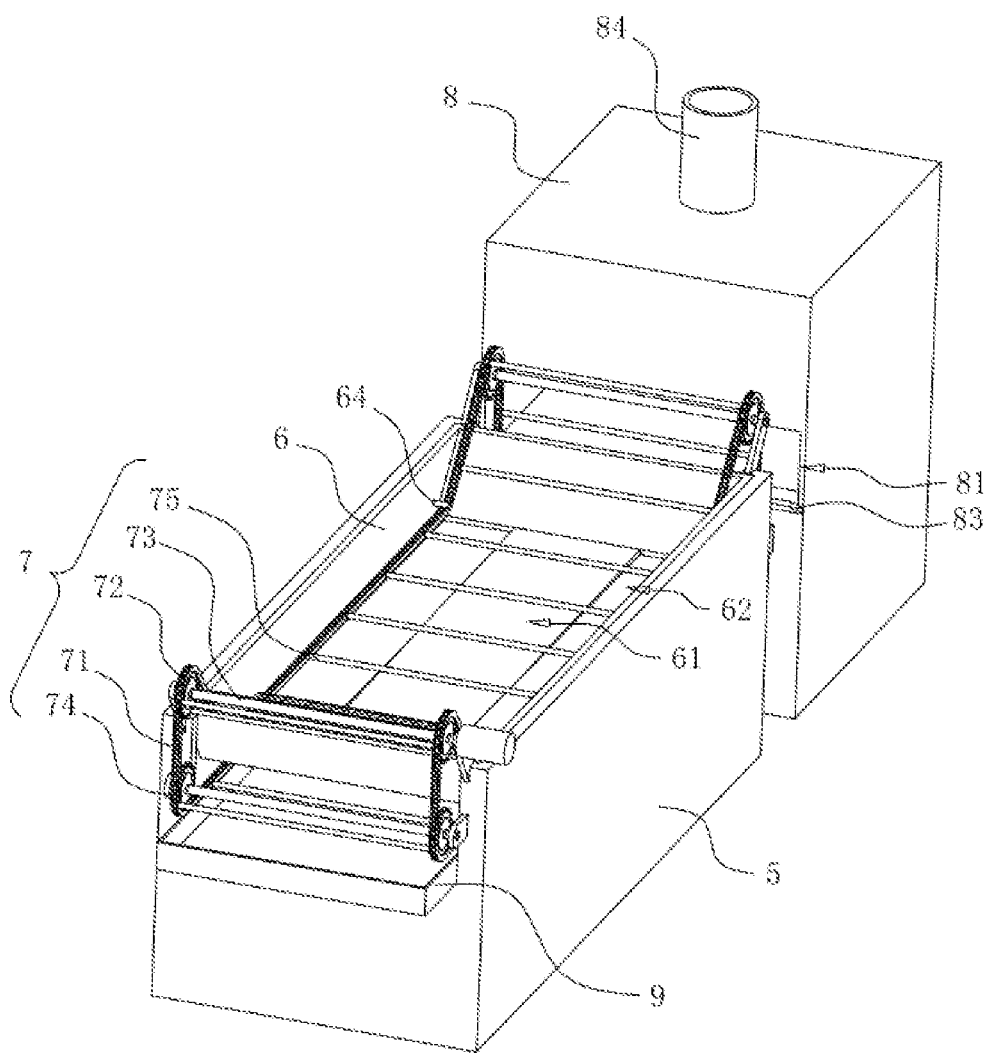
FIG. 5 is a schematic structural diagram of the heating device in Embodiment 3 of the present application.

Referring to FIG. 5, the heating device includes a cuboid heating box 5 with an opening on an upper end face, and two side walls along the length direction of the heating box 5 are provided with gaps. The heating box 5 is fixedly connected with a storage tank 6, and the storage tank 6 has a length that is equal to the length of the heating box 5, and has an opening that is upwards as the heating box 5. Ends of the storage tank 6 are located at the gap of the heating box 5. The storage tank 6 is provided with a drive assembly 7 configured for driving the can fixing cage from one gap to the other gap.

The drive assembly 7 includes two transmission chains 71, and the two transmission chains 71 are arranged on two sides of the storage tank 6. The transmission chains 71 surround the outside of the storage tank 6 through two gaps, a first side of the transmission chain 71 is located above the storage tank 6, and a second side of the transmission chain 71 is located below the storage tank 6. A transmission sprocket 72 corresponding to the transmission chain 71 is provided outside two ends of the storage tank 6 and near the gap. The transmission sprocket 72 is engaged with the inner side of the transmission chain 71. A connecting rod 73 are rotatably connected at two ends of the heating box 5 near the gap, and the connecting rod 73 runs through the center of two transmission sprockets 72 on the same side, and is fixedly connected with two transmission sprockets 72. A driving motor is fixedly connected on the heating box 5, and the output shaft of the driving motor is coaxially fixed with the end of one of the connecting rods 73.

A tensioning sprocket 74 is provided below the transmission sprocket 72, and the tensioning sprocket 74 is connected with the heating box 5 with identical structure as the transmission sprocket 72. The tensioning sprocket 74 is engaged with the inner side of transmission chain 71, such that the transmission chain 71 is arranged around the storage tank 6 under the support of the transmission sprocket 72 and the tensioning sprocket 74.

The sidewalls of the two ends of the storage tank 6 near the gap are configured to be inclined, so that the opening of the storage tank 6 is larger than the bottom of the storage tank 6. A guide block 64 is fixed to the inner wall of the storage tank 6 near the bottom of the storage tank 6, and the outer side of the transmission chain 71 abuts against the lower side of the guide block 64, so that the transmission chain 71 moves along the inner wall of the storage tank 6 and parallel to the storage tank 6. A plurality of pushing components 75 evenly spaced are arranged between the two transmission chains 71, and the can fixing cage is placed between two adjacent pushing components 75.

Hot oil are added in the storage tank 6. In this embodiment, the hot oil is edible oil. When the transmission chain 71 is driven to rotate by the drive motor, the can fixing cage is pushed by the pushing component 75, so that the can fixing cage can move along the moving direction of the transmission chain 71, during which the cans 3 are rapidly heated by the hot oil.

In this embodiment, the pushing component 75 is a pushing rod, and the two ends of the pushing rod are respectively fixed on the two transmission chains 71. When the transmission chain 71 moves, the pushing rod abuts against the lower outer sidewall of the can fixing cage, thereby driving the can fixing cage to roll.

The pushing component 75 can further be provided with a pushing plate, two ends of the pushing plate are fixedly connected with the two transmission chains 71, and the pushing plate is configured to be inclined to facilitate supporting and lifting the can fixing cage.

A plurality of temperature sensors uniformly spaced are arranged inside the storage tank 6, along the conveying direction of the transmission chain 71. Meanwhile, heaters corresponding to the temperature sensors are installed on the lower outer wall of the storage tank 6. When the temperature of the hot oil detected by the temperature sensor is lower than a preset temperature range, the heater at the corresponding position is started, so as to quickly increase the oil temperature, maintain the hot oil within a certain temperature range, and improve the stability of the overall process.

Furthermore, in order to balance the overall oil temperature and reduce the possibility of large fluctuations of local oil temperature, a first oil guide groove 61 is formed in the lower inner wall of the storage tank 6. The first oil guide groove 61 is parallel to the transmission chain 71 and is located at the middle part of the storage tank 6. Two second oil guide grooves 62 located on two sides of the first oil guide groove 61, respectively, are formed in the lower inner wall of the storage tank 6, and the first oil guide groove 61 and the second oil guide groove 62 are configured to be parallel with each other. Along the conveying direction of the transmission chain 71, the first oil guide groove 61 has a gradually decreasing groove depth, and the second oil guide groove 62 has a gradually increasing groove depth.

When the can fixing cage is placed in the first oil guide groove 61 and rolls along the first oil guide groove 61, the hot oil in the first oil guide groove 61 is driven to move with the can fixing cage, and at this time, the hot oil at the shallower part of the second oil guide groove 62 flows to the deeper part of the first oil guide groove 61, and the hot oil flows from the deeper part of the second oil guide groove 62 to the shallower part of the second oil guide groove 62. Therefore, when the cans moves, the hot oil circulates in the storage tank 6, thereby reducing fluctuation in the temperature of the hot oil.

An oil tray 9 is arranged below the storage tank 6 and the transmission chains 71, and the two ends of the oil tray 9 are lapped on the lower edge of the gap, respectively, so as to receive the oil dripped from above.

Figure 6:
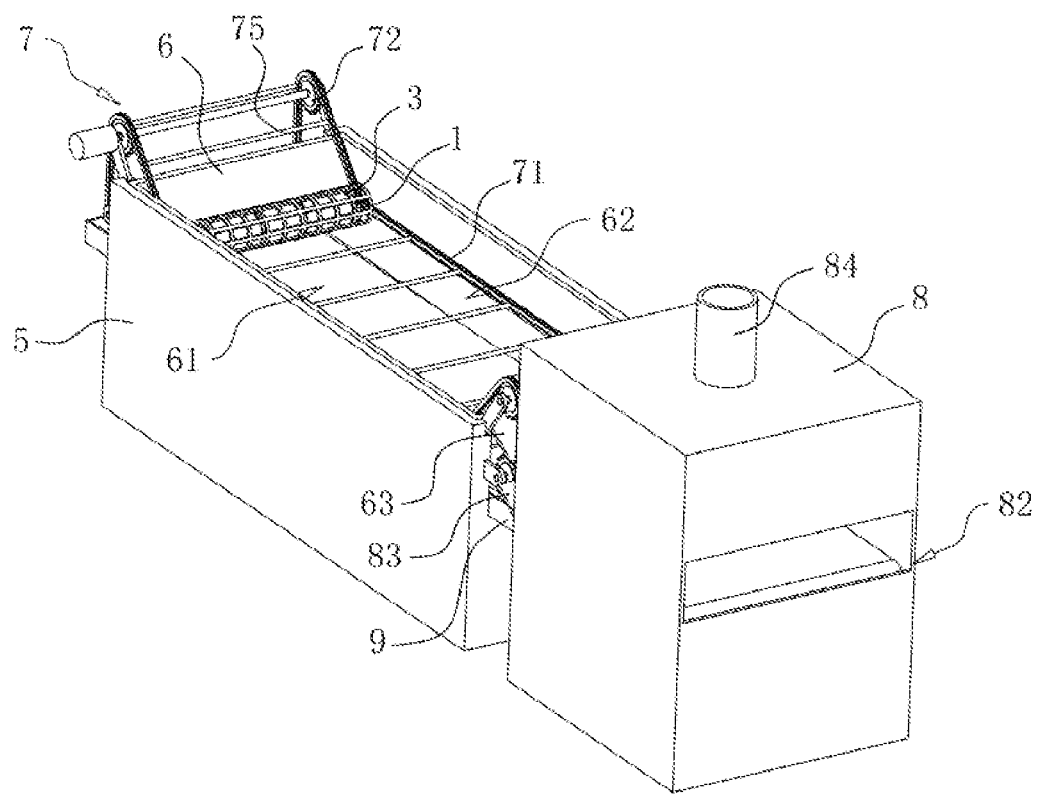
FIG. 6 is a structural schematic diagram showing the connection relationship between the transition box and the heating box.

Referring to FIG. 5 and FIG. 6, along the conveying direction of the transmission chain 71, a transition box 8 is provided downstream of the heating box 5, and the transition box 8 is configured to be a closed box. A feed port 81 is provided in the transition box 8 at a first side close to the heating box 5, and a discharge port 82 is provided in the transition box 8 at a second side far away from the heating box 5. A conveyer belt is provided between the feed port 81 and the discharge port 82, and the transition box 8 is provided with a ventilation pipe 84. The ventilation pipe 84 is configured for being connected to a blower, such that hot wind or cold wind can be passed into the transition box 8.

A deflector 63 inclined downward is fixed to a side of the storage tank 6 close to the transition box 8, and the deflector 63 is located below the connecting rod 73. Moreover, a lower side wall of the feed port 81 is provided with a guide plate 83, one end of the guide plate 83 away from the feed port 81 is configured to be inclined upward, and the guide plate 83 is lower than the deflector 63. During the rotation process of the transmission chain 71, the pushing component 75 passes between the guide plate 83 and the deflector 63, and the can fixing cage rolls onto the guide plate 83 along the deflector 63, enters the transition box 8, is conveyed by the conveyor belt, and leaves the discharge port 82.

The implementation principle of Embodiment 3 is as follows: the can fixing cage is put into the storage tank 6 and heated by the hot oil. The transmission chain 71 is driven to rotate by the driving motor, so that the can fixing cage is driven to roll by the pushing component 75. After the can fixing cage enters the transition box 8, an insulation treatment is carried out by the transition box 8 until the food in the cans 3 is mature and qualified.

The embodiment of the present application also discloses a method for heating and sterilizing cans, including the following steps:

Step 1: placing one or more cans 3 in the cage body 1 sequentially along an axial direction, and clamping the one or more cans 3 in the cage body 1 by the cage cover 2; in particular, the adjacent cans 3 are separated by pad blocks 4;

Step 2: adding hot oil in the storage tank 6, and maintaining an oil temperature by using the heater;

Step 3: placing the can fixing cage in the storage tank 6, and driving the pushing component 75 to move, thereby driving the can fixing cage to roll in the storage tank 6 by the driving motor, until the cage body 1 enters the transition box 8;

Step 4: conveying the can fixing cage in the transition box 8, and introducing hot air or cold air into the transition box 8 through the ventilation pipe 84 to maintain the one or more cans 3 inside the can fixing cage at an appropriate temperature, until the can fixing cage leaves the transition box 8 through the discharge port 82; and Step 5: taking out the one or more cans 3 from the can fixing cage, and cleaning the one or more cans 3.

All of the above are preferred embodiments of the present application, and are not intended to limit the protection scope of the present application. Therefore, all equivalent changes made according to the structure, shape, and principle of the present application should fall within the protection scope of the present application.

LISTING OF REFERENCE SIGNS 1. cage body;
11. sliding slot;
12. connecting bolt;
13. limit groove;
2. cage cover;
21. positioning block;
22. limit block;

23. fixing bolt;
3. can;
4. pad block;
41. support block;
42. abutting block;
43. slider;
5. heating box;
6. storage tank;
61. first oil guide groove;
62. second oil guide groove;
63. deflector;
64. guide block;
7. drive assembly;
71. transmission chain;
72. transmission sprocket;
73. connecting rod;
74. tensioning sprocket;
75. pushing component;
8. transition box;
81. feed port;
82. discharge port;
83. guide plate;
84. ventilation pipe;
9. oil tray.

What is claimed is:

1. A method for heating and sterilizing cans using a heating device for heating a can fixing cage, comprising the following steps:

Step 1: placing one or more cans in a cage body successively along an axis direction, and clamping the one or more cans in the cage body by a cage cover;

Step 2: adding hot oil in a storage tank, and maintaining an oil temperature by using a heater;

Step 3: placing the cage body in the storage tank, and driving the cage body to roll in the storage tank by a drive assembly until the cage body enters a transition box;

Step 4: conveying the cage body in the transition box, and introducing hot air or cold air into the transition box through a ventilation pipe to maintain the one or more cans inside the cage body at a specified temperature, until the cage body leaves the transition box through a discharge port; and Step 5: taking out the one or more cans from the cage body, and cleaning the one or more cans; wherein the heating device for heating the can fixing cage comprises a heating box with an opening on an upper end face, wherein the storage tank is provided inside the heating box, the can fixing cage is arranged in the storage tank, the drive assembly configured for driving a movement of the can fixing cage is provided in the storage tank, the heater is provided below the storage tank, the can fixing cage comprises the cage body configured for holding the one or more cans, the cage body has an opening at one end, the can fixing cage further comprises the cage cover configured for sealing the opening of the cage body, the cage cover and the cage body are detachably connected, both ends of the one or more cans abut against pad blocks, the one or more cans are fixed by the pad blocks in the cage body, the drive assembly comprises a transmission chain, a first side of the transmission chain is located above the storage tank, a second side of the transmission chain is located below the storage tank, transmission sprockets configured for meshing with an inner side of the transmission chain are provided outside two ends of the storage tank, the heating box is provided with a drive motor configured for driving the transmission sprockets to rotate, a plurality of pushing components distributed evenly are provided on the transmission chain, the can fixing cage is located between two adjacent pushing components of the plurality of pushing components, a first oil guide groove parallel to the transmission chain is formed in an inner bottom wall of the storage tank, second oil guide grooves are further formed in the inner bottom wall of the storage tank at both sides of the first oil guide groove, the first oil guide groove and the second oil guide grooves are configured to be parallel with each other, the first oil guide groove has a gradually decreasing groove depth from a first end to a second end of the first oil guide groove, and each of the second oil guide grooves has a gradually increasing groove depth from a first end to a second end of a corresponding second oil guide groove of the second oil guide grooves.

\* \* \* \* \*